United States Patent [19]

Dumas et al.

[11] Patent Number: 5,547,869
[45] Date of Patent: Aug. 20, 1996

[54] PLASMIDS

[75] Inventors: Bruno Dumas, Paris; Monica Gervais, Saint Leu la Foret; Max Bergoin, Saint Christophe lez Ales; Mireille Jourdan, Moliere sur Ceze; Francoise X. Jousset, Saint Christophe lez Ales, all of France

[73] Assignee: Roussel Uclaf, France

[21] Appl. No.: 195,814

[22] Filed: Feb. 14, 1994

Related U.S. Application Data

[63] Continuation of Ser. No. 881,054, May 11, 1992, abandoned, which is a continuation-in-part of Ser. No. 278,735, Dec. 2, 1988, abandoned.

[30] Foreign Application Priority Data

Dec. 3, 1987 [FR] France .................................... 87 16764

[51] Int. Cl.⁶ .......................... C12N 15/00; C12N 15/34; C12N 15/35

[52] U.S. Cl. .................................. 435/252.33; 435/320.1; 530/23.72

[58] Field of Search .............................. 435/320.1, 235, 435/252.33, 172.3; 536/23.72; 424/93 A; 935/9, 32, 73, 64

[56] References Cited

PUBLICATIONS

Bando et al, J. Virol. 61: 553 (1987).
Bolivar et al, Gene 2: 95 (1977).
Beaud et al, Chem. Abstr. 107: 148601v (1987).

*Primary Examiner*—James Martinell
*Attorney, Agent, or Firm*—Bierman and Muserlian

[57] ABSTRACT

Recombinant plasmids capable of replicating themselves in *Escherichia coli* containing a complete or partial sequence of the double or single strand DNA or a Densovirus causing a densovirosis in a sensitive insect, a process for obtaining said plasmids and a method of combatting ravager insects.

6 Claims, 5 Drawing Sheets

| | | | | | |
|---|---|---|---|---|---|
| NGTATTGCCA | CCGACGACGA | CGACGGCAGT | CCCTGCCGGC | GAAGCCGGCC | GCCGCGAAGC | 60
| GGCAAGGGAC | TGCCGTCGTC | GTCGTCGGTG | GCAATACTCG | TAGAGTATAA | GCAAGTACTC | 120
| AGCATGTATA | GAGTACTTGA | TGACGTCACG | GTGACCTTGA | CCTTTGACCT | TCTATATGAC | 180
| CTTGACCTAC | TTCTGTGACC | TTCTGGTCTA | CTGACCTTTG | ACCTTCTGAG | CTGATGTCTA | 240
| CTGACCTGAT | GATGGAGAGG | ATCCGAAGAC | CTTGGAGCTG | AAGGTGGAAC | ACAGGACCTG | 300
| ATGTTAGTGA | AGGACAGCAA | TAGTGTGCGA | GTGAGATAGC | ACTATAGCAA | CTGTTAGAGC | 630
| GAGATAGCAA | TATGAGTAAA | AGAGATAGCA | TGCAAACAAA | CCTTGAGATA | ATTTATGCGC | 420
| ATTTTATTAT | CTTGTTATTG | TGACCTCGTT | TGACCGGCAA | ACTCGCGTCG | AGGCTGGGCC | 480
| GTGTGCAAAA | CAGGATGTGG | CTGGCCAGCG | GACCATTGAC | TATATAAAGG | CTGACGTGTT | 540
| CTATTTTTAG | TCAGTATGTC | TTTCTACACG | GCCGGGTTAA | TACATCGTGC | GCGACCCGGT | 600
| TATCGTATTA | TACCAGAAAG | TACTGCTACT | GAAGATATTG | AACTTGGTGC | TATTGGAGAA | 660
| GAAACTCCAT | TATTAAGTGA | AGGTGCTGTT | ACTGCTGTAG | AAGAAAGTGC | TGCTGTTGGT | 720
| TTACCAGAAC | TTGGTGCTGG | ACTTGCTGGT | GCTATTGGAA | CACATGCTGA | CGTATTGTAT | 780
| AGAAATAGAA | ACGTTTTTAA | AAGTGTTTTA | ACTGGAAATT | ATACCGATTT | AAAAGGCAAT | 840
| CCTTTAAAAC | AACGAAACGC | TATTTCTGAA | AAAACTAAAC | AACTTGGAAG | AGGAATATTT | 900
| CAAGGCGATT | TCAACCGTGC | ATTTCCTGAT | GATTTAAAAT | TGGAAACTGA | CAAGAAAAA | 960
| AAAGATTTAC | TACGTTATTA | TAATCACAAT | AGAAGATTAG | CTGGATTAAG | TGAAGCTTAT | 1020
| CCACAAGGGA | AAGGATACGC | TTATGCTAAA | AGTCAAAAAG | TATTAGAAGC | TGAACGACGA | 1080
| GGATTAACTG | TTCCCGGATA | TAAATATCTT | GGTCCTGGAA | ATTCACTTAA | CAGAGGTCAA | 1140
| CCTACTAATC | AAATAGACGA | AGACGCTAAG | GAACACGACG | AAGCATACGA | TAAAGCGAAA | 1200
| ACAAGTCAAG | AAGTAAGTCA | AGCAGATAAT | ACATTTGTCA | ATAAAGCGTT | AGATCACATA | 1260
| GTTAATGCTA | TCAATCTTAA | AGAAACTCCT | GGTAACGCTT | TTGGAGCTGC | TATCGGAGCT | 1320
| ATTGGAATTG | AACTAAGCA | AGCTATCGAA | AAACACAGTG | GAGTAATCTA | CCCTTCTGTT | 1380
| TCAGGTATGT | CCCGTCAAAT | TAATTCTAAA | TACTTAAATA | GCTGGCATGA | CTGGATTGAG | 1440
| CAAAATAAAC | ATAATAATTT | TGAAGGAATA | CAATTACCAG | AGGACTTTTA | CACAGAAGAA | 1500
| CAAACTCTTT | CAGATTCACC | GATGTCAGAG | GGAACAAAAC | GTAAAGCTGA | TACTCCTGTT | 1560
| GAAGAAGGTC | CTTCTAAAAA | AGGTGCTCAT | AACGCTCCAC | ATAACTCGCA | AGGTACAGAT | 1620
| CCTCAAAATC | CTAGTTCTTC | CGGAGCAACT | ACTTCTMTTG | ACGTTGAAAT | GGCTATGTCA | 1680
| TTACCTGGAA | CTGGTTCTGG | AACATCATCT | GGAGGAGGCA | ACACTTCAGG | TCAAGAGGTT | 1740
| TATGTAATTC | CTCGTCCATT | TTCGAACTTT | GGTAAAAAAT | TAAGTACTTA | TACAAAGTCT | 1800
| CATAAATTTA | TGATATTTGG | TCTTGCCAAT | AATGTTATTG | GACCTACAGG | TACTGGTACA | 1860
| ACAGCTGTAA | ATCGTTTAAT | TACAACTTGT | TTGGCTGAAA | TTCCATGGCA | GAAATTGCCT | 1920
| TTGTATATGA | ACCAATCTGA | ATTTGATTTA | TTACCTCCTG | GTAGTAGAGT | AGTTGAATGT | 1980

FIG. IA

```
AATGTTAAAG TAATATTCAG AACTAATCGT ATTGCATTTG AGACTAGTTC AACTGCTACT    2040
AAACAAGCTA CATTGAATCA AATATCTAAT TTACAAACTG CTGTTGGATT AAATAAACTT    2100
GGATGGGGTA TTGATAGATC ATTTACTGCT TTTCAATCAG ATCAACCTAT GATTCCCACT    2160
GCTACTAGTG CACCAAAATA TGAACCTATA ACTGGTACGA CTGGTTATAG AGGTATGATA    2220
GCTGATTATT ATGGTGCTGA TTCTACTAAT GATGCTGCAT TTGGTAATGC TGGTAACTAT    2280
CCTCATCATC AAGTTGGTTC ATTTACTTTT ATTCAAAATT ATTATTGTAT GTATCAACAA    2340
ACCAATCAAG GTACTGGAGG TTGGCCATGT TTAGCTGAAC ATCTTCAACA ATTTGATTCT    2400
AAAACTGTTA ATAATCAATG TTTAATTGAT GTAACTTATA AACCTAAAAT GGGTTTAATT    2460
AAACCACCGT TAAATTATAA AATTATTGGT CAACCTACTG CAAAAGGTAC TATATCTGTT    2520
GGTGATAATT TAGTTAACAT GCGAGGAGCT GTTGTAATAA ATCCACCTGA AGCAACACAA    2580
TCTGTTACTG AATCAACTCA TAATTTGACT CGCAATTTTC CAGCTAATTT GTTTAATATT    2640
TATTCTGACA TTGAAAAATC TCAAATTTTA CATAAAGGAC CTTGGGGACA CGAAAATCCA    2700
CAGATACAAC CAAGTGTTCA TATTGGTATT CAAGCTGTAC CAGCATTAAC TACAGGAGCT    2760
TTACTTGTAA ATTCAAGTCC TTTAAATTCA TGGACTGATT CTATGGGTTA TATTGATGTT    2820
ATGTCTAGTT GTACTGTTAT GGAATCTCAG CCTACACACT TTCCATTTTC GACTGATGCT    2880
AATACTAACC CTGGTAATAC CATTTATCGT ATTAATCTTA CACCGAACTC TCTTACTAGT    2940
GCTTTCAATG GATTGTACGG TAATGGAGCT ACTCTTGGTA ACGTTTAAAT AAAACAATAA    3000
TGTATCCCAT AACCATTTAT TAAAATGTAA TATTATATTT ACTCAATAAA AGGAAAAATG    3060
TCATTGGATG TGGTTTCAAT TCATAATCCT TTAAGAATGG CGCAGCATTC CACTTGTATT    3120
GAATAATTCT ATCACTAAAA GCAGTTTCAT ACATAAAAGG TACAGTATTA TTAGTAAGTA    3180
TTATAACTGG AGTGCGTTTT ACATGTGCAT CCATACGATT TTTAACTCTA ACAGTATAAG    3240
GATCTCCTCC AAACATCATT TTAATTGTAT CAGTTAAAGA ACTCTCATAG TTAGGTTCAT    3300
TCCATAATAA TACACGTTTA TTAGGTGCTT CTTGAAATGC AAACAAGTTA TGTCTATTAG    3360
CTTGACCTAA CTGACCATAA GATAGTAATA ATCCAAAGAT CATATCAAAA AAGAAATTTT    3420
TACCAGCACT TGGAGGAGAT ATAATAAGAA AAGCATTTAA CTTAGGTATA CGACGGTCTA    3480
ATACATTGAC CAAATTAGTA AGAAACTCTA CAATTAAATC TTCATCATCA TTACATTGAA    3540
ATTTAAGTAA TTCTATAATA ATATTCAAAG AATTCTCAAG ATTATCATAT TTCATAGAAG    3600
AAATAAACAA AGCATATGGA TTAAGTTCTT GTTCATCAGT AAAATTATAA TCTTCAGTAA    3660
GTAAATTATA AATTTCTCTC AAAGACATAG CATTTAAATC CTTACCAAAG TCATCGCATG    3720
CTGCTTGTAT ATAATCACGA TTTTTAGGAT CACATAACAA ATCATCATCA CGAAATTCTG    3780
GCACATACA TATAGCACTC ACTGGAGACA CATAATATTT TCTTAATAAC GCTTTTGTCT    3840
TTTTCCGTAT GTATGCGAAT TTCCCTGCCG AATAGGCTTT CTTTTCATAA AGTCTTCCGT    3900
TAGAACTGCC AGCATCTGAT CTACGGCTAA TTTTGTGCTC TTGCTGTTCA CACTCATAGT    3960
```

FIG. 1B

```
AATCCGTGCA ATCGGAGCTT GATACCATTT CTCTTTCTTT AAACTCTCTG GTCCATCGTA    4020
CACATTCATC GTTACTCGGT ATTTTCCCAC TTTCTCCTCT AACGTATATT GCACGCTCTC    4080
CCCGTTTTCG TACAAAGAAA TAGATGAAGA CATCGTACCA GTCTGTTCGC TTGAATTCCC    4140
AGATGAATTT GACTGGTTTG CCAGTTTTCT GAACAGATCC GAAGGGCTTG ACTTGACTAA    4200
TCCAGATGTC CCTGCAACTG CGATTGGTGT AAGAGCAATC GTGGATGACG TGGATGTGAT    4260
CTCCTTCTTC AGAAAATCCG AACAGTCCGT TTCGTCTACT TCTTCCGTAC TCACGCAAGA    4320
CGTCCAAACA TTGATCACGG AGCTGAATAT CTCGTAAGAT AATGACATCG CTGATATATG    4380
CGCTGGAAGG TTTAATACTT TGCCCAGTAA CGTATCCAAA GAATTCACTG CCCATTTTTT    4440
CCAGTTCTTC TGCCATATAT TGAAAGTTTT CTTGAGATTC TTTTGCAATG CTGGCCATTG    4500
TTCCTCGTCC TCCATGTGAC CATTCACGTT TTCTAGATGT ATTTGCCACC ATGCTACATT    4560
GTTCACTAGG GGATGTTCTT CCTGAAGACT CTCGTATAAT GTCTTGATTA GGTCTGGTAG    4620
TACTATCGGT TTCTCTGTTG GTGTCTCCAT TGTTCATCTG TAATTAATGT CTACTATTAG    4680
GATGTTTTAC ATAAAAACTA TTAGACATAT ATTCGTCCTC TTCTGAACTA CTTGAGTATC    4740
TCCTTTTTTT ATTAGGAGAG TTTTCATAAA TTACAGATAT ATTAAACAAT GGACAAGTAT    4800
GACATATTTG ACACCAACTA CTACCATCTT GTAATCTATT TATAATATCT TCAGCATCTT    4860
CTACGAACAC AGTTCTATTA TACATAAATC TGTATTCATC TGGATCTTCA CAATTAGTAT    4920
AACAAAATTT ACAAATTTTC CACATAGTTT TAAAGGGCTT TCCATTCATA TTCCATGCAT    4980
TAAATTCATC AGTATCATAA GGGTCTCTAT GGTTAATTAA TTCTTTAAAA TAATACACAC    5040
ATTCTATCAG CATAGTTTCA TCTAACCATT CAGGTATTTC ATTTAASTGC ATAACAGCTA    5100
AATATAACTG GAAAGGTAAT CTGTTTTGTT TTGTCCAATC CCAGTGTTCT AATTCTTCCA    5160
TAGCTAAAGT ATGATCTATG TCTTCTCCAC AAGCAATAAT CTGATTATCT AGATCATGCT    5220
GCATATTAAG TATAGGTTTA GGCAAAATTG ACAAGTCTAG ACCATTAAGT CTAGCAGTCT    5280
TATAAGCCTC ATAGAACAAA GACTTTGGAT TGTACACTTT TTCAAATAAA CGAACGAACA    5340
CAAAGAAACC TGGCAATAGA CATACCGATT ATATTCTGGA ACCACTTTTG CACAACACTA    5400
CTTTTTCACT GAGATGTTCA CTCGACGACT GCTGCTCGTA GACTGATGAT GGCGCTCTGC    5460
TGTTATCTCT ATTTATAGCC AATGGTCCGC TGGCCAGCCA CATCCTGTTT TGCACACGGC    5520
CCAGCCTCGA CGCGAGTTTG CCGGTCAAAC GAGGTCACAA TAACAAGATA ATAAAATGCG    5580
CATAAATTAT CTCAAGGTTT GTTTGCATGC TATCTCTTYT ACTCATATTG CTATCTCGCT    5640
CTAACAGTTG CTATAGTGCT ATCTCACTCG CACACTATTG CTGTCCTTCA CTAACATCAG    5700
GTCCTGTGTT CCACCTTCAG CTCCAAGGTC TTCGGATCCT CTCCATCATC AGGTCAGTAG    5760
ACCATCAGCT CAGAAGGTCA AAGGTCAGTA GACCAGAAGG TCACAGAAGT AGGTCAAGGT    5820
CATATAGAAG GTCAAAGGTC AAGGTCACCG TGACGTCATC AAGTACTCTA TACATGCTGA    5880
GTACTTGCTT ATACTCTACG AGTATTGCCN                                    5910
```

FIG. IC

The restriction enzymes Apa1, Bgl2, Cla1, Kpn1, Pst1, Pvu1, Sal1 & Sma1 have cleavage site in the genome of the DENSOVIRUS of JUNONIA

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
 ( A ) LENGTH: 5910
 ( B ) TYPE: NUCLEIC ACID
 ( C ) STRANDEDNESS: UNKNOWN
 ( D ) TOPOLOGY: UNKNOWN ( i i ) MOLECULE TYPE: cDNA ( i i i ) HYPOTHETICAL: NO ( v i ) ORIGINAL SOURCE:
 ( A ) ORGANISM: DENSOVIRUS
 ( B ) STRAIN: DENSOVIRUS OF JUNONIA
 ( C ) INDIVIDUAL ISOLATE:
 ( D ) DEVELOPMENTAL STAGE: LARVAE
 ( E ) HAPLOTYPE:
 ( F ) TISSUE TYPE:
 ( G ) CELL TYPE: SPODOPTERA LITTORALIS
 ( H ) CELL LINE:
 ( I ) ORGANELLE:

( i x ) FEATURE:
 ( B ) LOCATION: 1
 ( D ) OTHER INFORMATION: N IS A OR C OR G OR T,
 WHEREIN N IS ZERO TO 50 NUCLEOTIDES IN LENGTH ( i x ) FEATURE:
 ( B ) LOCATION: 1657
 ( D ) OTHER INFORMATION: M IS A OR C ( i x ) FEATURE:
 ( B ) LOCATION: 5619
 ( D ) OTHER INFORMATION: Y IS C OR T ( i x ) FEATURE:
 ( B ) LOCATION: 5910
 ( D ) OTHER INFORMATION: N IS A OR C OR G OR T,
 WHEREIN N IS ZERO TO 130 NUCLEOTIDES IN LENGTH ( x i ) SEQUENCE DESCRIPTION: SEQ ID NO: 1:

```
NGTATTGCCA CCGACGACGA CGACGGCAGT CCCTGCCGGC GAAGCCGGCC GCCGCGAAGC   60
GGCAAGGGAC TGCCGTCGTC GTCGTCGGTG GCAATACTCG TAGAGTATAA GCAAGTACTC  120
AGCATGTATA GAGTACTTGA TGACGTCACG GTGACCTTGA CCTTTGACCT TCTATATGAC  180
CTTGACCTAC TTCTGTGACC TTCTGGTCTA CTGACCTTTG ACCTTCTGAG CTGATGTCTA  240
CTGACCTGAT GATGGAGAGG ATCCGAAGAC CTTGGAGCTG AAGGTGGAAC ACAGGACCTG  300
ATGTTAGTGA AGGACAGCAA TAGTGTGCGA GTGAGATAGC ACTATAGCAA CTGTTAGAGC  360
GAGATAGCAA TATGAGTAAA AGAGATAGCA TGCAAACAAA CCTTGAGATA ATTTATGCGC  420
ATTTTATTAT CTTGTTATTG TGACCTCGTT TGACCGGCAA ACTCGCGTCG AGGCTGGGCC  480
GTGTGCAAAA CAGGATGTGG CTGGCCAGCG GACCATTGAC TATATAAAGG CTGACGTGTT  540
CTATTTTTAG TCAGTATGTC TTTCTACACG GCCGGGTTAA TACATCGTGC GCGACCCGGT  600
TATCGTATTA TACCAGAAAG TACTGCTACT GAAGATATTG AACTTGGTGC TATTGGAGAA  660
GAAACTCCAT TATTAAGTGA AGGTGCTGTT ACTGCTGTAG AAGAAAGTGC TGCTGTTGGT  720
TTACCAGAAC TTGGTGCTGG ACTTGCTGGT GCTATTGGAA CACATGCTGA CGTATTGTAT  780
AGAAATAGAA ACGTTTTTAA AAGTGTTTTA ACTGGAAATT ATACCGATTT AAAAGGCAAT  840
CCTTTAAAAC AACGAAACGC TATTTCTGAA AAAACTAAAC AACTTGGAAG AGGAATATTT  900
```

```
CAAGGCGATT TCAACCGTGC ATTTCCTGAT GATTTAAAAT TGGAAACTGA ACAAGAAAAA  960
AAAGATTTAC TACGTTATTA TAATCACAAT AGAAGATTAG CTGGATTAAG TGAAGCTTA 1020
CCACAAGGGA AAGGATACGC TTATGCTAAA AGTCAAAAAG TATTAGAAGC TGAACGACG 1080
GGATTAACTG TTCCCGGATA TAAATATCTT GGTCCTGGAA ATTCACTTAA CAGAGGTCA 1140
CCTACTAATC AAATAGACGA AGACGCTAAG GAACACGACG AAGCATACGA TAAAGCGAA 1200
ACAAGTCAAG AAGTAAGTCA AGCAGATAAT ACATTTGTCA ATAAAGCGTT AGATCACAT 1260
GTTAATGCTA TCAATCTTAA AGAAACTCCT GGTAACGCTT TTGGAGCTGC TATCGGAGC 1320
ATTGGAATTG GAACTAAGCA AGCTATCGAA AAACACAGTG GAGTAATCTA CCCTTCTGT 1380
TCAGGTATGT CCCGTCAAAT TAATTCTAAA TACTTAAATA GCTGGCATGA CTGGATTGA 1440
CAAAATAAAC ATAATAATTT TGAAGGAATA CAATTACCAG GGACTTTTA CACAGAAGA 1500
CAAACTCTTT CAGATTCACC GATGTCAGAG GGAACAAAAC GTAAAGCTGA TACTCCTGT 1560
GAAGAAGGTC CTTCTAAAAA AGGTGCTCAT AACGCTCCAC ATAACTCGCA AGGTACAGA 1620
CCTCAAAATC CTAGTTCTTC CGGAGCAACT ACTTCTMTTG ACGTTGAAAT GGCTATGTC 1680
TTACCTGGAA CTGGTTCTGG AACATCATCT GGAGGAGGCA ACACTTCAGG TCAAGAGGT 1740
TATGTAATTC CTCGTCCATT TTCGAACTTT GGTAAAAAAT TAAGTACTTA TACAAAGTC 1800
CATAAATTTA TGATATTTGG TCTTGCCAAT AATGTTATTG GACCTACAGG TACTGGTAC 1860
ACAGCTGTAA ATCGTTTAAT TACAACTTGT TTGGCTGAAA TTCCATGGCA GAAATTGCC 1920
TTGTATATGA ACCAATCTGA ATTTGATTTA TTACCTCCTG GTAGTAGAGT AGTTGAATG 1980
AATGTTAAAG TAATATTCAG AACTAATCGT ATTGCATTTG AGACTAGTTC AACTGCTAC 2040
AAACAAGCTA CATTGAATCA AATATCTAAT TTACAAACTG CTGTTGGATT AAATAAACT 2100
GGATGGGGTA TTGATAGATC ATTTACTGCT TTTCAATCAG ATCAACCTAT GATTCCCAC 2160
GCTACTAGTG CACCAAAATA TGAACCTATA ACTGGTACGA CTGGTTATAG AGGTATGAT 2220
GCTGATTATT ATGGTGCTGA TTCTACTAAT GATGCTGCAT TTGGTAATGC TGGTAACTA 2280
CCTCATCATC AAGTTGGTTC ATTTACTTTT ATTCAAAATT ATTATTGTAT GTATCAACA 2340
ACCAATCAAG GTACTGGAGG TTGGCCATGT TTAGCTGAAC ATCTTCAACA ATTTGATTC 2400
AAAACTGTTA ATAATCAATG TTTAATTGAT GTAACTTATA AACCTAAAAT GGGTTTAAT 2460
AAACCACCGT TAAATTATAA AATTATTGGT CAACCTACTG CAAAAGGTAC TATATCTGT 2520
GGTGATAATT TAGTTAACAT GCGAGGAGCT GTTGTAATAA ATCCACCTGA AGCAACACA 2580
TCTGTTACTG AATCAACTCA TAATTTGACT CGCAATTTTC CAGCTAATTT GTTTAATAT 2640
TATTCTGACA TTGAAAAATC TCAAATTTTA CATAAGGAC CTTGGGGACA CGAAAATCC 2700
CAGATACAAC CAAGTGTTCA TATTGGTATT CAAGCTGTAC CAGCATTAAC TACAGGAGC 2760
TTACTTGTAA ATTCAAGTCC TTTAAATTCA TGGACTGATT CTATGGGTTA TATTGATGT 2820
ATGTCTAGTT GTACTGTTAT GGAATCTCAG CCTACACACT TTCCATTTTC GACTGATGC 2880
AATACTAACC CTGGTAATAC CATTTATCGT ATTAATCTTA CACCGAACTC TCTTACTAG 2940
GCTTTCAATG GATTGTACGG TAATGGAGCT ACTCTTGGTA ACGTTTAAAT AAAACAATA 3000
TGTATCCCAT AACCATTTAT TAAAATGTAA TATTATATTT ACTCAATAAA AGGAAAAAT 3060
TCATTGGATG TGGTTTCAAT TCATAATCCT TTAAGAATGG CGCAGCATTC CACTTGTAT 3120
GAATAATTCT ATCACTAAAA GCAGTTTCAT ACATAAAAGG TACAGTATTA TTAGTAAGT 3180
TTATAACTGG AGTGCGTTTT ACATGTGCAT CCATACGATT TTTAACTCTA ACAGTATAA 3240
GATCTCCTCC AAACATCATT TTAATTGTAT CAGTTAAAGA ACTCTCATAG TTAGGTTCA 3300
```

```
TCCATAATAA TACACGTTTA TTAGGTGCTT CTTGAAATGC AAACAAGTTA TGTCTATTA 3360
CTTGACCTAA CTGACCATAA GATAGTAATA ATCCAAAGAT CATATCAAAA AAGAAATTT 3420
TACCAGCACT TGGAGGAGAT ATAATAAGAA AAGCATTTAA CTTAGGTATA CGACGGTCT 3480
ATACATTGAC CAAATTAGTA AGAAACTCTA CAATTAAATC TTCATCATCA TTACATTGA 3540
ATTTAAGTAA TTCTATAATA ATATTCAAAG AATTCTCAAG ATTATCATAT TTCATAGAA 3600
AAATAAACAA AGCATATGGA TTAAGTTCTT GTTCATCAGT AAAATTATAA TCTTCAGTA 3660
GTAAATTATA AATTTCTCTC AAAGACATAG CATTTAAATC CTTACCAAAG TCATCGCAT 3720
CTGCTTGTAT ATAATCACGA TTTTTAGGAT CACATAACAA ATCATCATCA CGAAATTCT 3780
GCACATCACA TATAGCACTC ACTGGAGACA CATAATATTT TCTTAATAAC GCTTTTGTC 3840
TTTTCCGTAT GTATGCGAAT TTCCCTGCCG AATAGGCTTT CTTTTCATAA AGTCTTCCG 3900
TAGAACTGCC AGCATCTGAT CTACGGCTAA TTTTGTGCTC TTGCTGTTCA CACTCATAG 3960
AATCCGTGCA ATCGGAGCTT GATACCATTT CTCTTTCTTT AAACTCTCTG GTCCATCGT 4020
CACATTCATC GTTACTCGGT ATTTTCCCAC TTTCTCCTCT AACGTATATT GCACGCTCT 4080
CCCGTTTTCG TACAAAGAAA TAGATGAAGA CATCGTACCA GTCTGTTCGC TTGAATTCC 4140
AGATGAATTT GACTGGTTTG CCAGTTTTCT GAACAGATCC GAAGGGCTTG ACTTGACTA 4200
TCCAGATGTC CCTGCAACTG CGATTGGTGT AAGAGCAATC GTGGATGACG TGGATGTGA 4260
CTCCTTCTTC AGAAAATCCG AACAGTCCGT TCGTCTACT  TCTTCCGTAC TCACGCAAG 4320
CGTCCAAACA TTGATCACGG AGCTGAATAT CTCGTAAGAT AATGACATCG CTGATATAT 4380
CGCTGGAAGG TTTAATACTT TGCCCAGTAA CGTATCCAAA GAATTCACTG CCCATTTTT 4440
CCAGTTCTTC TGCCATATAT TGAAAGTTTT CTTGAGATTC TTTTGCAATG CTGGCCATT 4500
TTCCTCGTCC TCCATGTGAC CATTCACGTT TTCTAGATGT ATTTGCCACC ATGCTACAT 4560
GTTCACTAGG GGATGTTCTT CCTGAAGACT CTCGTATAAT GTCTTGATTA GGTCTGGTA 4620
TACTATCGGT TTCTCTGTTG GTGTCTCCAT TGTTCATCTG TAATTAATGT CTACTATTA 4680
GATGTTTTAC ATAAAAACTA TTAGACATAT ATTCGTCCTC TTCTGAACTA CTTGAGTAT 4740
TCCTTTTTTT ATTAGGAGAG TTTTCATAAA TTACAGATAT ATTAAACAAT GGACAAGTA 4800
GACATATTTG ACACCAACTA CTACCATCTT GTAATCTATT TATAATATCT TCAGCATCT 4860
CTACGAACAC AGTTCTATTA TACATAAATC TGTATTCATC TGGATCTTCA CAATTAGTA 4920
AACAAAATTT ACAAATTTTC CACATAGTTT TAAAGGGCTT TCCATTCATA TTCCATGCA 4980
TAAATTCATC AGTATCATAA GGGTCTCTAT GGTTAATTAA TTCTTTAAAA TAATACACA 5040
ATTCTATCAG CATAGTTTCA TCTAACCATT CAGGTATTTC ATTTAAATGC ATAACAGCT 5100
AATATAACTG GAAAGGTAAT CTGTTTTGTT TTGTCCAATC CCAGTGTTCT AATTCTTCC 5160
TAGCTAAAGT ATGATCTATG TCTTCTCCAC AAGCAATAAT CTGATTATCT AGATCATGC 5220
GCATATTAAG TATAGGTTTA GGCAAAATTG ACAAGTCTAG ACCATTAAGT CTAGCAGTC 5280
TATAAGCCTC ATAGAACAAA GACTTTGGAT TGTACACTTT TTCAAATAAA CGAACGAAC 5340
CAAAGAAACC TGGCAATAGA CATACCGATT ATATTCTGGA ACCACTTTTG CACAACACT 5400
CTTTTTCACT GAGATGTTCA CTCGACGACT GCTGCTCGTA GACTGATGAT GGCGCTCTG 5460
TGTTATCTCT ATTTATAGCC AATGGTCCGC TGGCCAGCCA CATCCTGTTT TGCACACGG 5520
CCAGCCTCGA CGCGAGTTTG CCGGTCAAAC GAGGTCACAA TAACAAGATA ATAAAATGC 5580
CATAAATTAT CTCAAGGTTT GTTTGCATGC TATCTCTTYT ACTCATATTG CTATCTCGC 5640
CTAACAGTTG CTATAGTGCT ATCTCACTCG CACACTATTG CTGTCCTTCA CTAACATCA 5700
```

```
GTCCTGTGTT  CCACCTTCAG  CTCCAAGGTC  TTCGGATCCT  CTCCATCATC  AGGTCAGTA 5760

ACCATCAGCT  CAGAAGGTCA  AAGGTCAGTA  GACCAGAAGG  TCACAGAAGT  AGGTCAAGG 5820

CATATAGAAG  GTCAAAGGTC  AAGGTCACCG  TGACGTCATC  AAGTACTCTA  TACATGCTG 5880

GTACTTGCTT  ATACTCTACG  AGTATTGCCN                                   5910
```

PLASMIDS

PRIOR APPLICATION

This application is a continuation of U.S. patent application Ser. No. 881,054 filed May 11, 1992, now abandoned which is a continuation-in-part of U.S. patent application Ser. No. 278,735 filed Dec. 2, 1988, now abandoned.

STATE OF THE ART

Densonucleoses are diseases affecting a large number of invertebrates, mainly insects, which are caused by the Densoviruses. The term densonucleose reflects the hypertrophy characteristic of the nuclei in which the Densovirus multiplies and under conditions, a mortality approaching 100% can be reached in 4 or 5 days. These viruses, classified in the genus Densovirus, constitute, with the two genera Parvovirus and Dependovirus or parvovirus of vertebrates, the Parvoviridae family.

The Densoviruses are small isometric viruses, not enveloped, with DNA, strongly pathogenic for many species of ravager insects of economic importance, notably the lepidoptera, in which they were originally discovered. In the natural environment, they are responsible for epizooties which effectively take part in the regulation of the populations of their hosts. Up to the present, some twenty Densoviruses have been isolated from insects of different groups: lepidoptera, diptera, orthoptera and dictyoptera originating from all regions of the globe.

The Densoviruses offer, therefore, very interesting possibilities for use against insects of economic importance and notably lepidoptera, this new means of microbiological combat being capable of substituting for chemical combat or supplementing it. In addition, it is important to emphasize that, despite their great virulence against insects, preliminary trials and many years of laboratory experiments have not shown any pathogenic effect in man. Preparations based on other entomopathogenic viruses such as the baculovirus are marketed at present.

The methods of industrial production of these viruses, which rely on infection of insects bred in large quantities, incur high production costs. Attempts at mass production of these virus in cell cultures have come up against the same problems of cost. As for the baculoviruses, multiplication of the Densoviruses is normally obtained on larvae (Ann. Rev. Entomol., 1979, Vol. 24: pages 63–87), which implies a high production cost. Furthermore, many strains of Densoviruses cannot be multiplied on their hosts, taking into account the great difficulties met in setting up the artificial media necessary for industrial breeding.

It was therefore of great interest to find other ways of production of infectious material, not requiring the intervention of multiplication on the host. The possibility exists of obtaining this production of the Densovirus by genetic engineering and in fact, the size of their genome is compatible with an insertion in a bacterial plasmid, while this cannot be envisaged for a virus with a genome of very high molecular weight such as the baculovirus.

Also relevant prior art is Journal of Virology, Vol. 61 No. 2, February 1987, p. 553–560, Archives of Virology, Vol. 93 No. 1, 2, January, 1987, p. 139–146 and Comptes rendus de L'Acad. des. Sc. de Paris, Vol. 299 No 20 III (1984), p. 889–894.

OBJECTS OF THE INVENTION

It is an object of the invention to provide novel recombinant plasmids capable of reproducing themselves in *Escherichia coli* containing a complete or partial sequence of double or single strand DNA of a Densovirus causing a densovirosis in sensitive insect and a method of producing the said plasmids.

It is another object of the invention to provide a novel method of combatting ravager insects.

These and other objects and advantages of the invention will become obvious from the following detailed description.

THE INVENTION

The novel recombinant plasmids of the invention capable of replicating themselves in *Escherichia coli* contain a complete or partial sequence of double or single strand DNA of a Densovirus causing a densovirosis in a sensitive insect. All the Densoviruses of which a complete or partial sequence of DNA is contained in the plasmids of the invention are cited in "Intervirology", 23:61–73 (1985). The Densoviruses of ravager lepidoptera which have been most studied are the Junonia, Galleria and Agraulis Densoviruses.

Therefore, the invention is particularly concerned with plasmids that contain a complete or partial double or single strand sequence of a Densovirus of Junonia, Galleria or Agraulis and particularly, with the plasmids that contain a complete or partial sequence of double or single strand of the DNA of the Densovirus of Junonia (J-DNV). These latter plasmids are hereafter called pJ in the test.

The genome of the Densovirus is a linear single strand molecule of DNA of 5000 to 6000 bases. During the viral morphogenesis, the virions of the Densovirus indifferently encapsulate the + chains and the − chains, but always separately and in equimolecular proportion. Extraction of DNA under conditions of high ionic strength (0.1 SSC) from such a viral population leads to the formation of double stranded molecules by the pairing of complementary chains. [Truffaut et al (1967) and Arch. Ges. Virusforsch. 21, 469–474, and Barvise et al I.O., (1970). FEBS lett. 6, 13–16]. Thus, by their low molecular weight and their property of forming bicatenary chains, these genomes lend themselves particularly well to their integration in plasmids. It must be emphasized that the bicatenary DNA extracted from the virions is infectious, just as much in cellular cultures as by transfection of larvae of the sensitive species. [JOUSSET, 1st Congr. Soc. Fr. Microbiol., Toulouse (France), April 1986, CP59, p. 44, and JOUSSET, Soc. Invertebr. Pathol., 1986, p. 121. Colloq. Invertebr., Veldhoven (The Netherlands), August 1986]. The cloning of the bicatenary DNA of the Densovirus of Junonia has thus been realized and is described further on in the experimental part.

The sequence of the cloned genome has been determined by the usual methods [Sanger et al. (1977) Proc. Nat. Acad. Sci. USA Vol. 74 p. 5463—Maxam et al (1980), Methods Enzymol Vol. 65 p. 499]. Thus the invention also has as its subject the complete sequence of the viral genome of the Densovirus J-DNV corresponding to SEQ ID NO. 1 which is as follows:

NGTATTGCCA CCGACGACGA CGACGGCAGT CCCTGCCGGC GAAGCCGGCC GCCGCGAAGC 60
GGCAAGGGAC TGCCGTCGTC GTCGTCGGTG GCAATACTCG TAGAGTATAA GCAAGTACTC 120
AGCATGTATA GAGTACTTGA TGACGTCACG GTGACCTTGA CCTTTGACCT TCTATATGAC 180
CTTGACCTAC TTCTGTGACC TTCTGGTCTA CTGACCTTTG ACCTTCTGAG CTGATGTCTA 240
CTGACCTGAT GATGGAGAGG ATCCGAAGAC CTTGGAGCTG AAGGTGGAAC ACAGGACCTG 300

ATGTTAGTGA AGGACAGCAA TAGTGTGCGA GTGAGATAGC ACTATAGCAA CTGTTAGAGC 630
GAGATAGCAA TATGAGTAAA AGAGATAGCA TGCAAACAAA CCTTGAGATA ATTTATGCGC 420
ATTTTATTAT CTTGTTATTG TGACCTCGTT TGACCGCAA ACTCGCGTCG AGGCTGGGCC 480
GTGTGCAAAA CAGGATGTGG CTGGCCAGCG ACCATTGAC TATATAAAGG CTGACGTGTT 540
CTATTTTTAG TCAGTATGTC TTTCTACACG GCCGGGTTAA TACATCGTGC GCGACCCGGT 600
TATCGTATTA TACCAGAAAG TACTGCTACT GAAGATATTG AACTTGGTGC TATTGGAGAA 660
GAAACTCCAT TATTAAGTGA AGGTGCTGTT ACTGCTGTAG AAGAAAGTGC TGCTGTTGGT 720
TTACCAGAAC TTGGTGCTGG ACTTGCTGGT GCTATTGGAA CACATGCTGA CGTATTGTAT 780
AGAAATAGAA ACGTTTTAA AAGTGTTTTA ACTGGAAATT ATACCGATTT AAAAGGCAAT 840
CCTTTAAAAC AACGAAACGC TATTTCTGAA AAAACTAAAC AACTTGGAAG AGGAATATTT 900
CAAGGCGATT TCAACCGTGC ATTTCCTGAT GATTTAAAAT TGGAAACTGA ACAAGAAAAA 960
AAAGATTTAC TACGTTATTA TAATCACAAT AGAAGATTAG CTGGATTAAG TGAAGCTTAT 1020
CCACAAGGGA AAGGATACGC TTATGCTAAA AGTCAAAAAG TATTAGAAGC TGAACGACGA 1080
GGATTAACTG TTCCCGGATA TAAATATCTT GGTCCTGGAA ATTCACTTAA CAGAGGTCAA 1140
CCTACTAATC AAATAGACGA AGACGCTAAG GAACACGACG AAGCATACGA TAAAGCGAAA 1200
ACAAGTCAAG AAGTAAGTCA AGCAGATAAT ACATTTGTCA ATAAAGCGTT AGATCACATA 1260
GTTAATGCTA TCAATCTTAA AGAAACTCCT GGTAACGCTT TTGGAGCTGC TATCGGAGCT 1320
ATTGGAATTG GAACTAAGCA AGCTATCGAA AAACACAGTG GAGTAATCTA CCCTTCTGTT 1380
TCAGGTATGT CCCGTCAAAT TAATTCTAAA TACTTAAATA GCTGGCATGA CTGGATTGAG 1440
CAAAATAAAC ATAATAATTT TGAAGGAATA CAATTACCAG AGGACTTTA CACAGAAGAA 1500
CAAACTCTTT CAGATTCACC GATGTCAGAG GGAACAAAAC GTAAAGCTGA TACTCCTGTT 1560
GAAGAAGGTC CTTCTAAAAA AGGTGCTCAT AACGCTCCAC ATAACTCGCA AGGTACAGAT 1620
CCTCAAAATC CTAGTTCTTC CGGAGCAACT ACTTCTMTTG ACGTTGAAAT GGCTATGTCA 1680
TTACCTGGAA CTGGTTCTGG AACATCATCT GGAGGAGGCA ACACTTCAGG TCAAGAGGTT 1740
TATGTAATTC CTCGTCCATT TTCGAACTTT GGTAAAAAAT TAAGTACTTA TACAAAGTCT 1800
CATAAATTTA TGATATTTGG TCTTGCCAAT AATGTTATTG GACCTACAGG TACTGGTACA 1860
ACAGCTGTAA ATCGTTTAAT TACAACTTGT TTGGCTGAAA TTCCATGGCA GAAATTGCCT 1920
TTGTATATGA ACCAATCTGA ATTTGATTTA TTACCTCCTG GTAGTAGAGT AGTTGAATGT 1980
AATGTTAAAG TAATATTCAG AACTAATCGT ATTGCATTTG AGACTAGTTC AACTGCTACT 2040
AAACAAGCTA CATTGAATCA AATATCTAAT TTACAAACTG CTGTTGGATT AAATAAACTT 2100
GGATGGGTA TTGATAGATC ATTTACTGCT TTTCAATCAG ATCAACCTAT GATTCCCACT 2160
GCTACTAGTG CACCAAAATA TGAACCTATA ACTGTACGA CTGGTTATAG AGGTATGATA 2220
GCTGATTATT ATGGTGCTGA TTCTACTAAT GATGCTGCAT TTGGTAATGC TGGTAACTAT 2280
CCTCATCATC AAGTTGGTTC ATTTACTTTT ATTCAAAATT ATTATTGTAT GTATCAACAA 2340

ACCAATCAAG GTACTGGAGG TTGGCCATGT TTAGCTGAAC ATCTTCAACA ATTTGATTCT 2400
AAAACTGTTA ATAATCAATG TTTAATTGAT GTAACTTATA AACCTAAAAT GGGTTTAATT 2460
AAACCACCGT TAAATTATAA AATTATTGGT CAACCTACTG CAAAAGGTAC TATATCTGTT 2520
GGTGATAATT TAGTTAACAT GCGAGGAGCT GTTGTAATAA ATCCACCTGA AGCAACACAA 2580
TCTGTTACTG AATCAACTCA TAATTTGACT CGCAATTTTC CAGCTAATTT GTTTAATATT 2640
TATTCTGACA TTGAAAAATC TCAAATTTTA CATAAAGGAC CTTGGGGACA CGAAAATCCA 2700
CAGATACAAC CAAGTGTTCA TATTGGTATT CAAGCTGTAC CAGCATTAAC TACAGGAGCT 2760
TTACTTGTAA ATTCAAGTCC TTTAAATTCA TGGACTGATT CTATGGGTTA TATTGATGTT 2820
ATGTCTAGTT GTACTGTTAT GGAATCTCAG CCTACACACT TTCCATTTTC GACTGATGCT 2880
AATACTAACC CTGGTAATAC CATTTATCGT ATTAATCTTA CACCGAACTC TCTTACTAGT 2940
GCTTTCAATG GATTGTACGG TAATGGAGCT ACTCTTGGTA ACGTTTAAAT AAAACAATAA 3000
TGTATCCCAT AACCATTTAT TAAAATGTAA TATTATATTT ACTCAATAAA AGGAAAAATG 3060
TCATTGGATG TGGTTTCAAT TCATAATCCT TTAAGAATGG CGCAGCATTC CACTTGTATT 3120
GAATAATTCT ATCACTAAAA GCAGTTTCAT ACATAAAAGG TACAGTATTA TTAGTAAGTA 3180
TTATAACTGG AGTGCGTTTT ACATGTGCAT CCATACGATT TTTAACTCTA ACAGTATAAG 3240
GATCTCCTCC AAACATCATT TTAATTGTAT CAGTTAAAGA ACTCTCATAG TTAGGTTCAT 3300
TCCATAATAA TACACGTTTA TTAGGTGCTT CTTGAAATGC AAACAAGTTA TGTCTATTAG 3360
CTTGACCTAA CTGACCATAA GATAGTAATA ATCCAAAGAT CATATCAAAA AAGAAATTTT 3420
TACCAGCACT TGGAGGAGAT ATAATAAGAA AAGCATTTAA CTTAGGTATA CGACGGTCTA 3480
ATACATTGAC CAAATTAGTA AGAAACTCTA CAATTAAATC TTCATCATCA TTACATTGAA 3540
ATTTAAGTAA TTCTATAATA ATATTCAAAG AATTCTCAAG ATTATCATAT TTCATAGAAG 3600
AAATAAACAA AGCATATGGA TTAAGTTCTT GTTCATCAGT AAAATTATAA TCTTCAGTAA 3660
GTAAATTATA AATTTCTCTC AAAGACATAG CATTTAAATC CTTACCAAAG TCATCGCATG 3720
CTGCTTGTAT ATAATCACGA TTTTTAGGAT CACATAACAA ATCATCATCA CGAAATTCTG 3780
GCACATCACA TATAGCACTC ACTGGAGACA CATAATATTT CTTAATAAC GCTTTTGTCT 3840
TTTTCCGTAT GTATGCGAAT TTCCCTGCCG AATAGCTTT CTTTTCATAA AGTCTTCCGT 3900
TAGAACTGCC AGCATCTGAT CTACGGCTAA TTTTGTGCTC TTGCTGTTCA CACTCATAGT 3960
AATACGTGCA ATCGGAGCTT GATACCATTT CTCTTTCTTT AAACTCTCTG GTCCATCGTA 4020
CACATTCATC GTTACTCGGT ATTTTCCCAC TTTCTCCTCT AACGTATATT GCACGCTCTC 4080
CCCGTTTTCG TACAAAGAAA TAGATGAAGA CATCGTACCA GTCTGTTCGC TTGAATTCCC 4140
AGATGAATTT GACTGGTTTG CCAGTTTTCT GAACAGATCC GAAGGGCTTG ACTTGACTAA 4200
TCCAGATGTC CCTGCAACTG CGATTGGTGT AAGAGCAATC GTGGATGACG TGGATGTGAT 4260
CTCCTTCTTC AGAAAATCCG AACAGTCCGT TTCGTCTACT TCTTCCGTAC TCACGCAAGA 4320
CGTCCAAACA TTGATCACGG AGCTGAATAT CTCGTAAGAT AATGACATCG CTGATATATG 4380

CGCTGGAAGG TTTAATACTT TGCCCAGTAA
CGTATCCAAA GAATTCACTG CCCATTTTTT 4440
CCAGTTCTTC TGCCATATAT TGAAAGTTTT
CTTGAGATTC TTTTGCAATG CTGGCCATTG 4500
TTCCTCGTCC TCCATGTGAC CATTCACGTT TTCTA-
GATGT ATTTGCCACC ATGCTACATT 4560
GTTCACTAGG GGATGTTCTT CCTGAAGACT CTCG-
TATAAT GTCTTGATTA GGTCTGGTAG 4620
TACTATCGGT TTCTCTGTTG GTGTCTCCAT TGT-
TCATCTG TAATTAATGT CTACTATTAG 4680
GATGTTTTAC ATAAAAACTA TTAGACATAT
ATTCGTCCTC TTCTGAACTA CTTGAGTATC 4740
TCCTTTTTTT ATTAGGAGAG TTTTCATAAA TTACA-
GATAT ATTAAACAAT GGACAAGTAT 4800
GACATATTTG ACACCAACTA CTACCATCTT
GTAATCTATT TATAATATCT TCAGCATCTT 4860
CTACGAACAC AGTTCTATTA TACATAAATC TGTAT-
TCATC TGGATCTTCA CAATTAGTAT 4920
AACAAAATTT ACAAATTTTC CACATAGTTT
TAAAGGGCTT TCCATTCATA TTCCATGCAT 4980
TAAATTCATC AGTATCATAA GGGTCTCTAT GGT-
TAATTAA TTCTTTAAAA TAATACACAC 5040
ATTCTATCAG CATAGTTTCA TCTAACCATT CAGG-
TATTTC ATTTAAATGC ATAACAGCTA 5100
AATATAACTG GAAAGGTAAT CTGTTTTGTT TTGTC-
CAATC CCAGTGTTCT AATTCTTCCA 5160
TAGCTAAAGT ATGATCTATG TCTTCTCCAC AAG-
CAATAAT CTGATTATCT AGATCATGCT 5220
GCATATTAAG TATAGGTTTA GGCAAAATTG
ACAAGTCTAG ACCATTAAGT CTAGCAGTCT 5280
TATAAGCCTC ATAGAACAAA GACTTTGGAT TGTA-
CACTTT TTCAAATAAA CGAACGAACA 5340
CAAAGAAACC TGGCAATAGA CATACCGATT ATAT-
TCTGGA ACCACTTTTG CACAACACTA 5400
CTTTTTCACT GAGATGTTCA CTCGACGACT GCT-
GCTCGTA GACTGATGAT GGCGCTCTGC 5460
TGTTATCTCT ATTTATAGCC AATGGTCCGC TGGC-
CAGCCA CATCCTGTTT TGCACACGGC 5520
CCAGCCTCGA CGCGAGTTTG CCGGTCAAAC GAG-
GTCACAA TAACAAGATA ATAAAATGCG 5580
CATAAATTAT CTCAAGGTTT GTTTGCATGC
TATCTCTTYT ACTCATATTG CTATCTCGCT 5640
CTAACAGTTG CTATAGTGCT ATCTCACTCG CACAC-
TATTG CTGTCCTTCA CTAACATCAG 5700
GTCCTGTGTT CCACCTTCAG CTCCAAGGTC TTCG-
GATCCT CTCCATCATC AGGTCAGTAG 5760
ACCATCAGCT CAGAAGGTCA AAGGTCAGTA GAC-
CAGAAGG TCACAGAAGT AGGTCAAGGT 5820
CATATAGAAG GTCAAAGGTC AAGGTCACCG
TGACGTCATC AAGTACTCTA TACATGCTGA 5880
GTACTTGCTT ATACTCTACG AGTATTGCCN (SEQ ID
NO. 1) 5910

This represents the complete nucleotide sequence of the viral genome of the Densovirus J-DNV. N is the bases A or C or G or T wherein N is 0 to 50 nucleotides in length at location 1 and N is 0 to 130 nucleotides in length at location 5910. M is A or C and Y is C or T.

Also a part of the invention concepts the complete sequence of viral DNA of the Densovirus J-DNV corresponding to the sequence given above (SEQ ID NO. 1) wherein the two extremities N are eliminated.

BRIEF DESCRIPTION OF THE DRAWINGS

FIG. 1A–1C show the viral genome of the Densovirus J-DNV.

The invention is concerned particularly with the plasmids characterized in that they contain the complete sequence of the viral genome of the Densovirus J-DNV given above as well as the plasmids characterized in that they contain the complete or partial sequence of the double or single strand DNA of the Densovirus of Galleria. These plasmids are called pJ hereafter in the text. Among the pJ vectors defined above, the vector pBRJ is the preferred one. This plasmid contains the complete sequence of the viral DNA of the cloned Densovirus J-DNV corresponding to the sequence given above in which the two extremities N are eliminated. The principle of construction of the plasmid is given further on in the text and its construction is detailed in the experimental part.

The construction of the plasmids of the invention uses the known techniques utilized in this field. These techniques are described, for example, in Maniatis, Molecular Cloning: A Laboratory Manual, Cold Spring Harbor Laboratory (1982) or in "Basic methods in molecular biology", Davis—Dibner Battney—Elsevier (1986).

The starting vector used in the construction of the plasmids of the invention is preferably pBR 322, but any other classical cloning vector can be used, such as for example, the vector $PUC_{18}$ [Norrander, J. et al., Gene 26, 101–106 (1983)] or the vector $pAT_{153}$ [Twigg, A. J. and Sheratt D., Nature 283, 216–218 (1980)[.

Figure 2:
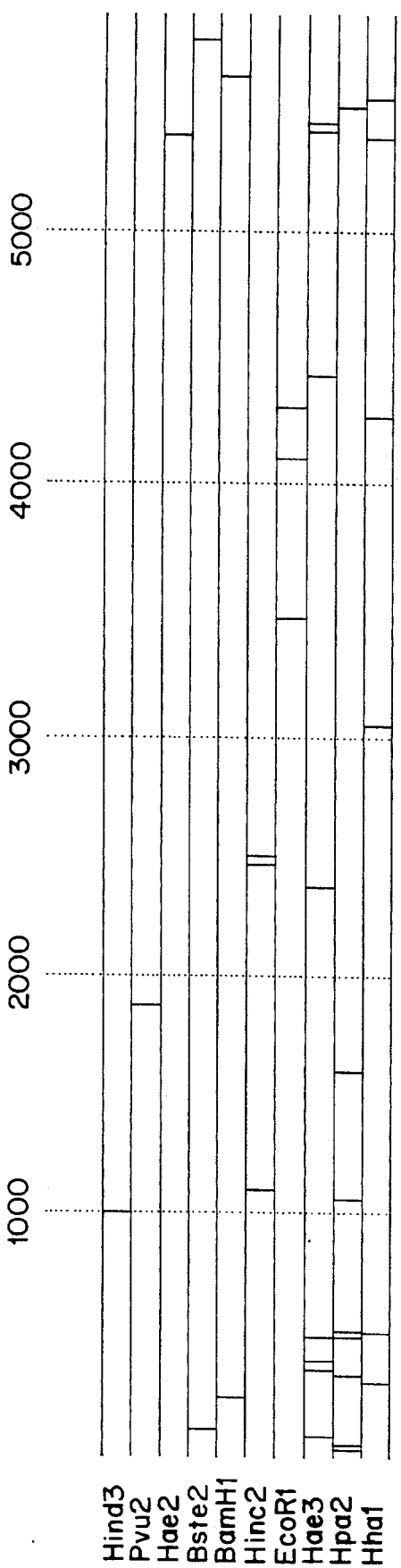
FIG. 2 shows a restriction map of Densovirus of Junonia.

The starting vector is digested by one or more restriction enzymes in a cloning site which is preferably a unique site. The choice of this site is dictated by prior knowledge concerning the cartography of the viral genome of the Densovirus. Thus, the pJ plasmids previously defined can be constructed from the starting vector pBR 322 digested by the enzymes generating free ends as, for example, ECoR V or NrUI or the enzymes generating sticky ends as, for example, PstI. These various possibilities derive from the cartography of the viral genome J-DNV given in FIG. 2. The same cloning strategy can, naturally, be applied to the other plasmids of the invention such as, for example, to the previously defined pJ plasmids which are constructed using the restriction enzyme PstI.

Figure 3:
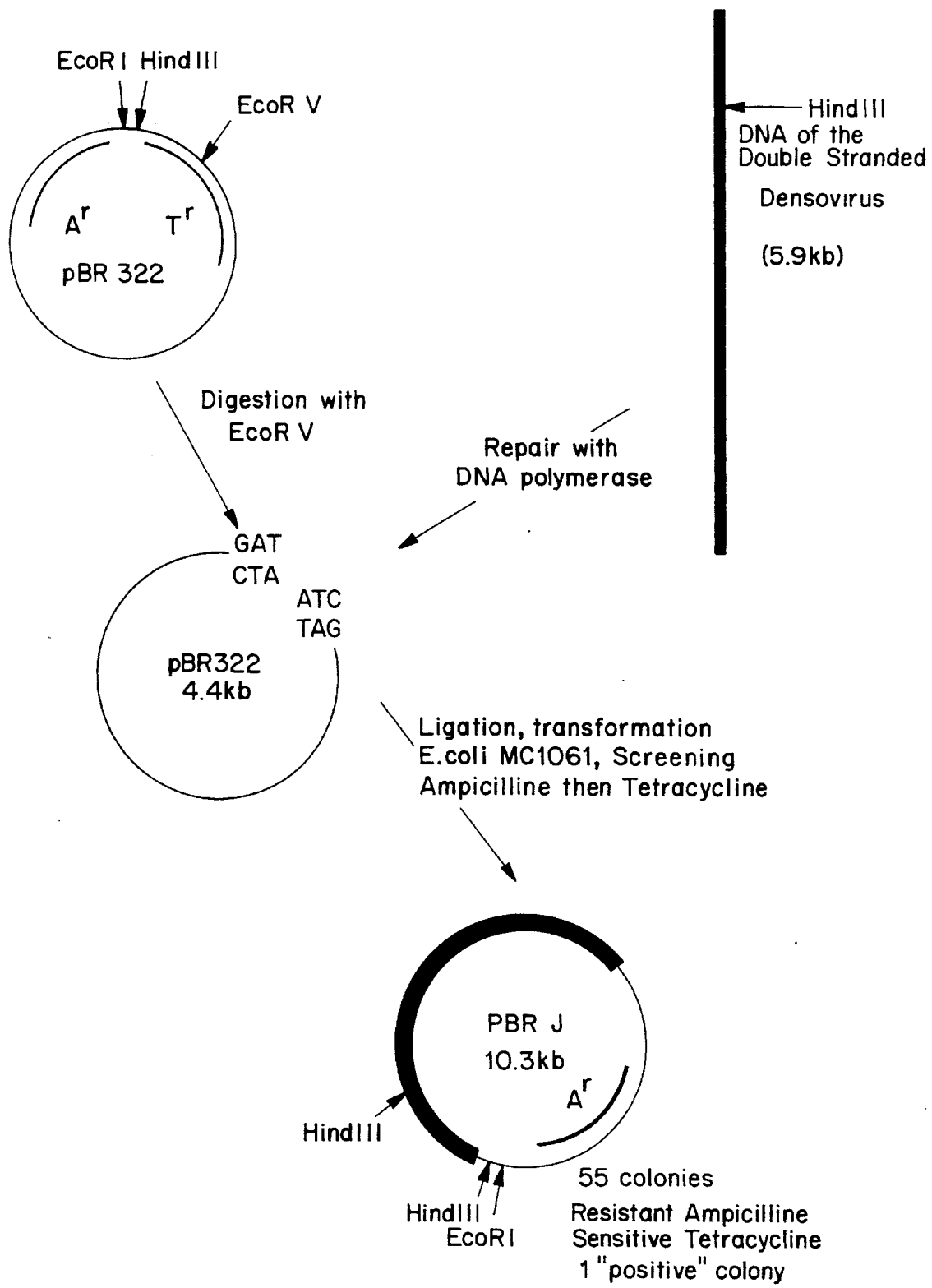
FIG. 3 shows the construction of pBRJ.

The construction of the preferred plasmid of the invention, the pBRJ plasmid, is detailed in FIG. 3. The viral DNA has been obtained from the Junonia virus by known techniques of extraction and purification. The purified DNA, after treatment with polymerase, is integrated at the unique site ECoRV of linearized pBR322. After transformation in *Escherichia coil,* only those colonies resistant to ampicillin and sensitive to tetracycline are selected.

Mini-lyses of recombinant bacteria are carried out to retain only the colonies containing the plasmids having inserted a fragment of size near to that of the genomic DNA. The scheme of construction of pBRJ is given in FIG. 3.

The invention is further concerned with the *Escherichia coli* host bacteria transformed by the recombinant plasmids capable of replicating themselves in *Escherichia coli,* characterized in that the contain a complete or partial sequence of double or single strand DNA of a Densovirus causing a densovirosis in a sensitive insect. It concerns particularly the bacteria transformed by the pJ plasmids and quite particularly by the pBRJ plasmid.

All the plasmids as defined above, and notably the pJ plasmids, and among these the plasmid pBRJ, can be used to combat ravager insects. The tests described in the experimental part show that the transfection by injection of the pBRJ plasmid in the hemolymph of larvae of Spodoptera enables the reproduction of a densovirosis identical to that caused by inoculation of the virion or of the viral J DNA. The same sensitivity to pBRJ has been shown on strains of Spodoptera resistant to chemical insecticides such as deltamethrine.

The invention is thus concerned with the method of combatting ravager insects biologically with the plasmids of the invention, and particularly the pJ plasmids, and among these, the plasmid pBRJ.

The insects of economic importance concerned in such usage are certain dipter vectors of medical and veterinary interest, and lepidopters and coleopters which are ravagers of food-producing and industrial crops such as cotton, corn, soya, oil-palm and bananas.

The invention also includes all the insecticidal formulations adapted for such use. The suitable formulations are those which enable the DNA to be coated with the plasmids of the invention. The vesicules coating this DNA must respond to several criteria: 1) hydrophilic internal cavity of sufficient diameter, 2) ensuring the protection of the DNA of the plasmid in the intestinal tract and 3) liberating their contents at the target cells, for example, those of the midintestine. Such vesicles are, for example, niosomes, liposomes, microcapsules of gelatin or of hydrosoluble polymers or of acrylamide or of any other type of microcapsule compatible with the criteria defined above. Forms of encapsulation in monocatenary phages of the M 13 type can also be envisaged.

The method of the invention for combatting ravager insect biologically comprises administering by ingestion an insecticidally effective amount of a plasmid of the invention.

In the following examples there are described several preferred embodiments to illustrate the invention but it should be understood that the invention is not intended to be limited to the specific embodiments.

EXAMPLE

Construction of the pBRJ plasmid
1) Purification of the DNA of the virus.
2) Cloning the DNA of the virus.
3) Sequence of the DNA of the virus.
4) Results of the transfections of the larvae of *Spodoptera littoralis* by the DNA of the Densovirus cloned or not in pBR 322.

Purification of the DNA
a) Purification of the Virus 20 to 30 *Spodoptera littoralis* larvae infected by the Densovirus of Junonia were ground up in a Potter dish in Tris HCl 0.1M pH 7.4 ascorbic acid 2% buffer and the product was clarified by centrifuging for 10 minutes at 10,000 g. The virions ere then agglomerated by centrifuging for 90 minutes at 35,000 rpm in an SW 41 rotor at 4° C. and the residue was taken up and deposited on a Renografin 20–76% gradient and centrifuged for 15 hours at 35,000 rpm in an SW 41 rotor. The band of virus localized in the lower third of the gradient was recovered and then dialyzed against buffer TE (tris HCl 10 mM EDTA 1 mM pH 8.0) for 3 days with a buffer change every 12 hours. The purity of the viral suspensions was then checked by electronic microscopy and UV spectrophotometry and their concentration was estimated by measurement of the optical density at 260 nm. One unit of optical density at 260 nm is equivalent to 100 µg of virion per ml.

b) Extraction of the DNA

The buffer of the viral suspension was adjusted to 4 mM EDTA at 100 µg of K proteinase per ml and at 2% sarkosyl. After an incubation of 2 hours at 37° C., the suspension was extracted three times with the same volume of phenol saturated with TE buffer. The aqueous phase was recovered and dialyzed against TE buffer. The DNA was then precipitated by addition of sodium acetate or lithium chloride at 0.2M final and two volumes of ethanol from 12 hours to 16 hours at –20° C. The DNA residue was rinsed three times with 70% alcohol and then taken up in TE buffer. The purity of the DNA viral solution was checked and its concentration determined by UV spectrometry.

2) Cloning the DNA of the Virus
a) Preparation of the DNA of the Virus

The extremities of the virus were repaired by the DNA polymerase of *E. coli* Klenow fragment. 3 µg of DNA of the virus were repaired in a volume of 75 µl with 7.5 U of DNA polymerase of *E. coli* (Boehringer Mannheim Biochemicals—BMB cat. No. 1014531). The repair buffer contained deoxyadenosine, deoxycytosine, guanosine and thymidine at a concentration of 40 uM, some $MgCl_2$ 5 mM, betamercaptoethanol 10 mM, beef albumin serum 100 ug/ml and Tris HCl 10 mM pH 7.5. The reaction mixture was incubated at 25° C. for one hour and after one hour at 65° C., the mixture was extracted with phenol-saturated Tris pH 78.5 0.1M, then precipitated in the presence of one volume of 0.3M acetate and two volumes of 100% ethanol.

b) Preparation of the DNA of the pBR322 Vector

The DNA of pBR322 was prepared by the method described by Maniatis et al Molecular Cloning: A Laboratory Manual, Cold Spring Harbor Laboratory (1982). 2.5 µg of DNA of pBR322 were digested by the restriction enzyme EcoRV under the conditions described by the BMB supplier using 18 U/µg of DNA of enzyme in a volume of 50 µl over 4 hours at 37° C. The digestion of the DNA was verified on a 1% agarose gel and the DNA was then dephosphorylated with alkaline phosphatase from the intestines of a calf. 2 µl of alkaline phosphatase BMB, cat. No. 713023 at 22 U/µl were added and after incubating for one hour at 37° C., the reaction was stopped by incubating for 45 minutes at 65° C. After extracting with saturated phenol Tris 0.1M pH 7.5, the aqueous phase was precipitated with ethanol in the presence of 0.3M acetate.

c) Ligation of the DNA of the Junonia Virus on the pBR322 Vector Linearized by the Restriction Enzyme EcoRV After precipitation and drying, the DNA of the vector was taken up at a concentration of 40 ng/µl and the DNA of the virus was taken up at a concentration of 1 µg/µl. The ligation was effected in a volume of 25 µl under the conditions described by the manufacturer (New England Biolabs). After incubating for one night at 4° C., the mixture was ready to transform the *Escherichia coli* bacteria (MC1061). (Casabadan M. J. Methods in Enzymol, (1983) 100 p. 293–3080).

d) Transformation of the Competent Bacteria

The competent bacteria were prepared by the procedure of Hanahan (Maniatis 1982) and preserved at –70° C. in the form of fractions of 200 µl. To 100 µl of competent bacteria thawed at 37° C., without exceeding 0° C., 1 µl of the preceding solution containing the DNA of the virus and the vector pBR322 were added.

After incubating for 15 minutes at 0° C. followed by a thermal shock of 5° to 37° C., there were added 900 ul of L B medium (10 g Bactotryptone DIFCO, 5 g of yeast extract DIFCO, 5 g of NaCl per liter, autoclaved at 120° C.). Recombinant bacteria were selected on dishes of L B agar medium containing 100 µg/ml of ampicillin. Out of 253 colonies resistant to ampicillin, 50 colonies sensitive to tetracycline were chosen.

e) Mini-lysis of the Recombinant Bacteria and Obtaining the pBRJ

Among these recombinant bacteria sensitive to tetracycline, only one carried the DNA of the cloned virus at the EcoRV site. Starting from a culture (1.5 ml) in L-B medium of each of the recombinant clones, the plasmidic DNA's were prepared by the alkaline method (Maniatis 1982). Each of the DNA's had been digested by the restriction enzyme EcoR1. One colony only carries a plasmidic DNA corresponding to a DNA of pBR322 with Junonia Densovirus inserted at the EcoRV site destroyed during the cloning. The corresponding pBRJ plasmid was prepared in a large quantity from a liter of culture at saturation in L-B medium by the method with sodium hydroxide and sodium dodecyl sulfate (Maniatis 1982). Digestions by the restriction enzymes BamH1, Pvu2, Bgl2, Nru1, Acc1, Pvu1, BstE2, Sph1, EcoR1, Hind3, Rsa1, Bgl1 enabled verification that the DNA of the Densovirus was inserted at the EcoRV site destroyed during the cloning in the orientation described in FIG. 3.

3) Sequence of the DNA of the Junonia Densovirus

The sequence of the DNA of the virus was determined for its greater part by Sanger's method (Sanger 1977). The junction virus pBR322 on the side of the Hind 3 site of PBR 322 was sequenced by the method of Maxam and Gilbert.

a) Sanger's Method
1) Random Cloning
Enzymatic Method

Random clonings were realized with the restriction enzymes:

Sau3a1, Xho2, Alu1, Hae3, Acc1. The DNA of the virus was digested by these restriction enzymes which cut the DNA of the Junonia Densovirus frequently to obtain fragments of the order of 100 pairs of bases (pb) at 1000 pb. The fragments obtained were sub-cloned in the vectors M13mp8 and M13mp9(Messing, J. and Viera, Gene, 19, 259–268 (1982) digested by the enzyme BamH1 (digestions Sau3A, Xho2), by the enzyme Sma1 (digestions Alu1, Hae3) and by the enzyme Acc1 (digestion Acc1).

Sonication Method

The DNA of the virus was sonicated until fragments on the order of 500 pb were obtained and the fragments obtained were repaired by the DNA polymerase of *E. coli* Klenow fragment by the process previously described. The fragments obtained were then sub-cloned in the vectors M13mp8 and M13mp9 digested by the enzyme Sma1.

2) Sub-cloning of Fragments Identified from the Restriction Cartography

Sub-cloning was done of the identified restriction fragments of which the size was less than 2000 pb obtained by digestions with the restriction enzymes (see restriction cartography in FIG. 1. BamH1, EcoR1, Hind3-BstE2, BstE2-BamH1, BstE2-Hind3, Hind3-Pvu2, Xba1-BstE2, Xba1, Hae3, Pvu2-Hae3, EcoR1-Xba1, Xba1-BstE2, Hae3-EcoR1, Hae3-Xba1, EcoR1-Pvu2, He3-BstE2. The fragments with a molecular weight of 110 pb to 2000 pb obtained by digestion with the above restriction enzymes were sub-cloned and then sequenced step by step using primers [Sanger (1977) Proc. Nat. Acad. Sci. USA Vol. 74 p. 5463; Biggin (1983) Proc. Nat. Acad. Sci. Vol. 80 p. 3963].

b) Method of Maxam and Gilbert

A fragment of 375 pb Hind 3 and BsteII near to the EcoR1 site of pBR322 proved to be impossible to sequence using Sanger's method. The sequence of this fragment was obtained from the Hind3 site and the BstE2 site by marking with T4 DNA polynucleotide kinase and ATP 32 P or with the DNA polymerase Klenow fragment and $dTT^{32}p$ or $dCT^{32}p$ (Maxam and Gilbert). The reactions were set to migrate on an acrylamide denaturising gel, urea [Sanger et al (1978), F.E.B.S. lett. Vol. 87, p. 107) in the presence of formamide at 40%.

c) Organization of the Sequences

The sequences obtained were entered in a computer of type Microvax2 and they were compared with the help of programs of the DB SYSTEM written by R. STADEN. [Nucleic Acids Research 12 (1) June 1987, p. 387–395]. After editing the sequences with the help of the edition program EDIT under VAX/VMS, the sequences were compared with the help of STADEN'S DBCOMP program and then they were organized with the help of the program DBUTIL. The sequence consensus obtained was that set forth above (SEQ ID NO. 1).

4) Results of the Transfections of the Larvae of *Spodoptera Littoralis* by DNA of the Densovirus Cloned or Not in pBR322 a) Process of Transfection by Inoculation

Different concentrations of DNA J or of pBRJ were inoculated to the young larvae of *Spodoptera littoralis* (stage 2 or 3 ) in a TE buffer, pH 8.0 (Tris 10 mM, EDTA 1 mM) with DEAE-dextran added (2 mg/ml final).

b) Surveillance of the Larvae

The transfected larvae and those of the control lots were raised individually on axenic medium at 25° C. Each day the dead larvae were removed, the data of nymphosis was noted and the nymphs were removed 6 days after nymphosis.

c) Control of the Transfected Insects

Each individual was ground up individually in 1 ml of PBS +2% of sodium azide and the grindings were clarified and the presence of virus was determined in the supernatants by the indirect ELISA method using anti-bodies titrated against Junonia Densovirus prepared on mice and anti-IgG of mice marked with peroxidase. Certain samples were checked with the electronic microscope.

d) Results

The transfection of the young larvae of *Spodoptera littoralis* by inoculation of DNAJ or DNA of pBRJ at concentrations of 30 ng of ADN-J per larva and of 56 ng of pBRJ/larva led to an infection percentage greater than 80% in the two cases. Comparable results were obtained by transfecting larvae of *Spodoptera littoralis* of Madagascan origin resistant to delta-methrin. Moreover, no infection appeared in the control lots inoculated either with the extraction buffer TE or with DNA pBR322 at a concentration of 30 ng to 1 ng/larva.

Example of Insecticide Composition

A composition of Liposome with base of 5 mg of phosphatidyl choline, 5 mg of phosphatidyl serine, 2.5 mg of cholesterol and 28 μg of pBRJ and sufficient Water q.s.p. of 1 ml was prepared.

Various modifications of the plasmids and methods of the invention may be made without departing from the spirit or scope thereof and it is to be understood that the invention is intended to be limited only as defined in the appended claims.

What is claimed is:

1. Recombinant plasmids capable of replicating themselves in *Escherichia coli* containing a complete sequence of the double or single strand DNA of a Densovirus (SEQ ID NO. 1) of Junonia (J-DNV) causing a densovirosis in a sensitive insect.

2. An *Escherichia coli* host bacterium transformed by a plasmid as defined in claim 1.

3. A complete sequence of the viral genome of the J-DNV Densovirus corresponding to sequence SEQ ID No. 1

GTATTGCCA CCGACGACBK CGACGGCAGT CCCTGCCGGC GAAGCCGGCC GCCGCGAAGC 60
GGCAAGGGAC TGCCGTCGTC GTCGTCGGTG GCAATACTCG TAGAGTATAA GCAAGTACTC 120
AGCATGTATA GAGTACTTGA TGACGTCACG GTGACCTTGA CCTTTGACCT TCTATATGAC 180
CTTGACCTAC TTCTGTGACC TTCTGGTCTA CTGACCTTTG ACCTTCTGAG CTGATGTCTA 240
CTGACCTGAT GATGGAGAGG ATCCGAAGAC CTTGGAGCTG AAGGTGGAAC ACAGGACCTG 300
ATGTTAGTGA AGGACAGCAA TAGTGTGCGA GTGAGATAGC ACTATAGCAA CTGTTAGAGC 630
GAGATAGCAA TATGAGTAAA AGAGATAGCA TGCAAACAAA CCTTGAGATA ATTTATGCGC 420
ATTTTATTAT CTTGTTATTG TGACCTCGTT TGACCGGCAA ACTCGCGTCG AGGCTGGGCC 480
GTGTGCAAAA CAGGATGTGG CTGGCCAGCG GACCATTGAC TATATAAAGG CTGACGTGTT 540
CTATTTTTAG TCAGTATGTC TTTCTACACG GCCGGGTTAA TACATCGTGC GCGACCCGGT 600
TATCGTATTA TACCAGAAAG TACTGCTACT GAAGATATTG AACTTGGTGC TATTGGAGAA 660
GAAACTCCAT TATTAAGTGA AGGTGCTGTT ACTGCTGTAG AAGAAAGTGC TGCTGTTGGT 720
TTACCAGAAC TTGGTGCTGG ACTTGCTGGT GCTATTGGAA CACATGCTGA CGTATTGTAT 780
AGAAATAGAA ACGTTTTTAA AAGTGTTTTA ACTGGAAATT ATACCGATTT AAAAGGCAAT 840
CCTTTAAAAC AACGAAACGC TATTTCTGAA AAAACTAAAC AACTTGGAAG AGGAATATTT 900
CAAGGCGATT TCAACCGTGC ATTTCCTGAT GATTTAAAAT TGGAAACTGA ACAAGAAAAA 960
AAAGATTTAC TACGTTATTA TAATCACAAT AGAAGATTAG CTGGATTAAG TGAAGCTTAT 1020
CCACAAGGGA AAGGATACGC TTATGCTAAA AGTCAAAAAG TATTAGAAGC TGAACGACGA 1080
GGATTAACTG TTCCCGGATA TAAATATCTT GGTCCTGGAA ATTCACTTAA CAGAGGTCAA 1140
CCTACTAATC AAATAGACGA AGACGCTAAG GAACACGACG AAGCATACGA TAAAGCGAAA 1200
ACAAGTCAAG AAGTAAGTCA AGCAGATAAT ACATTTGTCA ATAAAGCGTT AGATCACATA 1260
GTTAATGCTA TCAATCTTAA AGAAACTCCT GGTAACGCTT TTGGAGCTGC TATCGGAGCT 1320
ATTGGAATTG GAACTAAGCA AGCTATCGAA AAACACAGTG GAGTAATCTA CCCTTCTGTT 1380
TCAGGTATGT CCCGTCAAAT TAATTCTAAA TACTTAAATA GCTGGCATGA CTGGATTGAG 1440
CAAAATAAAC ATAATAATTT TGAAGGAATA CAATTACCAG AGGACTTTTA CACAGAAGAA 1500
CAAACTCTTT CAGATTCACC GATGTCAGAG GGAACAAAAC GTAAAGCTGA TACTCCTGTT 1560
GAAGAAGGTC CTTCTAAAAA AGGTGCTCAT AACGCTCCAC ATAACTCGCA AGGTACAGAT 1620
CCTCAAAATC CTAGTTCTTC CGGAGCAACT ACTTCTMTTG ACGTTGAAAT GGCTATGTCA 1680
TTACCTGGAA CTGGTTCTGG AACATCATCT GGAGGAGGCA ACACTTCAGG TCAAGAGGTT 1740
TATGTAATTC CTCGTCCATT TTCGAACTTT GGTAAAAAAT TAAGTACTTA TACAAAGTCT 1800
CATAAATTTA TGATATTTGG TCTTGCCAAT AATGTTATTG GACCTACAGG TACTGGTACA 1860
ACAGCTGTAA ATCGTTTAAT TACAACTTGT TTGGCTGAAA TTCCATGGCA GAAATTGCCT 1920
TTGTATATGA ACCAATCTGA ATTTGATTTA TTACCTCCTG GTAGTAGAGT AGTTGAATGT 1980
AATGTTAAAG TAATATTCAG AACTAATCGT ATTGCATTTG AGACTAGTTC AACTGCTACT 2040
AAACAAGCTA CATTGAATCA AATATCTAAT TTACAAACTG CTGTTGGATT AAATAAACTT 2100
GGATGGGGTA TTGATAGATC ATTTACTGCT TTTCAATCAG ATCAACCTAT GATTCCCACT 2160
GCTACTAGTG CACCAAAATA TGAACCTATA ACTGGTACGA CTGGTTATAG AGGTATGATA 2220
GCTGATTATT ATGGTGCTGA TTCTACTAAT GATGCTGCAT TTGGTAATGC TGGTAACTAT 2280
CCTCATCATC AAGTTGGTTC ATTTACTTTT ATTCAAAATT ATTATTGTAT GTATCAACAA 2340
ACCAATCAAG GTACTGGAGG TTGGCCATGT TTAGCTGAAC ATCTTCAACA ATTTGATTCT 2400
AAAACTGTTA ATAATCAATG TTTAATTGAT GTAACTTATA AACCTAAAAT GGGTTTAATT 2460
AAACCACCGT TAAATTATAA AATTATTGGT CAACCTACTG CAAAAGGTAC TATATCTGTT 2520
GGTGATAATT TAGTTAACAT GCGAGGAGCT GTTGTAATAA ATCCACCTGA AGCAACACAA 2580
TCTGTTACTG AATCAACTCA TAATTTGACT CGCAATTTTC CAGCTAATTT GTTTAATATT 2640
TATTCTGACA TTGAAAAATC TCAAATTTTA CATAAAGGAC CTTGGGGACA CGAAAATCCA 2700
CAGATACAAC CAAGTGTTCA TATTGGTATT CAAGCTGTAC CAGCATTAAC TACAGGAGCT 2760
TTACTTGTAA ATTCAAGTCC TTTAAATTCA TGGACTGATT CTATGGGTTA TATTGATGTT 2820
ATGTCTAGTT GTACTGTTAT GGAATCTCAG CCTACACACT TTCCATTTTC GACTGATGCT 2880
AATACTAACC CTGGTAATAC CATTTATCGT ATTAATCTTA CACCGAACTC TCTTACTAGT 2940
GCTTTCAATG GATTGTACGG TAATGGAGCT ACTCTTGGTA ACGTTTAAAT AAAACAATAA 3000
TGTATCCCAT AACCATTTAT TAAAATGTAA TATTATATTT ACTCAATAAA AGGAAAAATG 3060
TCATTGGATG TGGTTTGAAT TCATAATCCT TTAAGAATGG CGCAGCATTC CACTTGTATT 3120
GAATAATTCT ATCACTAAAA GCAGTTTCAT ACATAAAAGG TACAGTATTA TTAGTAAGTA 3180

TTATAACTGG AGTGCGTTTT ACATGTGCAT CCAT-
ACGATT TTTAACTCTA ACAGTATAAG 3240
GATCTCCTCC AAACATCATT TTAATTGTAT CAGT-
TAAAGA ACTCTCATAG TTAGGTTCAT 3300
TCCATAATAA TACACGTTTA TTAGGTGCTT
CTTGAAATGC AAACAAGTTA TGTCTATTAG 3360
CTTGACCTAA CTGACCATAA GATAGTAATA ATC-
CAAAGAT CATATCAAAA AAGAAATTTT 3420
TACCAGCACT TGGAGGAGAT ATAATAAGAA AAG-
CATTTAA CTTAGGTATA CGACGGTCTA 3480
ATACATTGAC CAAATTAGTA AGAAACTCTA CAAT-
TAAATC TTCATCATCA TTACATTGAA 3540
ATTTAAGTAA TTCTATAATA ATATTCAAAG AATTCT-
CAAG ATTATCATAT TTCATAGAAG 3600
AAATAAACAA AGCATATGGA TTAAGTTCTT
GTTCATCAGT AAAATTATAA TCTTCAGTAA 3660
GTAAATTATA AATTTCTCTC AAAGACATAG CATT-
TAAATC CTTACCAAAG TCATCGCATG 3720
CTGCTTGTAT ATAATCACGA TTTTTAGGAT CACAT-
AACAA ATCATCATCA CGAAATTCTG 3780
GCACATCACA TATAGCACTC ACTGGAGACA CAT-
AATATTT TCTTAATAAC GCTTTTGTCT 3840
TTTTCCGTAT GTATGCGAAT TTCCCTGCCG AATAG-
GCTTT CTTTTCATAA AGTCTTCCGT 3900
TAGAACTGCC AGCATCTGAT CTACGGCTAA
TTTTGTGCTC TTGCTGTTCA CACTCATAGT 3960
AATCCGTGCA ATCGGAGCTT GATACCATTT
CTCTTTCTTT AAACTCTCTG GTCCATCGTA 4020
CACATTCATC GTTACTCGGT ATTTTCCCAC
TTTCTCCTCT AACGTATATT GCACGCTCTC 4080
CCCGTTTTCG TACAAAGAAA TAGATGAAGA
CATCGTACCA GTCTGTTCGC TTGAATTCCC 4140
AGATGAATTT GACTGGTTTG CCAGTTTTCT GAA-
CAGATCC GAAGGGCTTG ACTTGACTAA 4200
TCCAGATGTC CCTGCAACTG CGATTGGTGT
AAGAGCAATC GTGGATGACG TGGATGTGAT 4260
CTCCTTCTTC AGAAAATCCG AACAGTCCGT
TTCGTCTACT TCTTCCGTAC TCACGCAAGA 4320
CGTCCAAACA TTGATCACGG AGCTGAATAT CTCG-
TAAGAT AATGACATCG CTGATATATG 4380
CGCTGGAAGG TTTAATACTT TGCCCAGTAA
CGTATCCAAA GAATTCACTG CCCATTTTTT 4440
CCAGTTCTTC TGCCATATAT TGAAAGTTTT
CTTGAGATTC TTTTGCAATG CTGGCCATTG 4500
TTCCTCGTCC TCCATGTGAC CATTCACGTT TTCTA-
GATGT ATTTGCCACC ATGCTACATT 4560
GTTCACTAGG GGATGTTCTT CCTGAAGACT CTCG-
TATAAT GTCTTGATTA GGTCTGGTAG 4620
TACTATCGGT TTCTCTGTTG GTGTCTCCAT TGT-
TCATCTG TAATTAATGT CTACTATTAG 4680
GATGTTTTAC ATAAAAACTA TTAGACATAT
ATTCGTCCTC TTCTGAACTA CTTGAGTATC 4740
TCCTTTTTTT ATTAGGAGAG TTTTCATAAA TTACA-
GATAT ATTAAACAAT GGACAAGTAT 4800

GACATATTTG ACACCAACTA CTACCATCTT
GTAATCTATT TATAATATCT TCAGCATCTT 4860
CTACGAACAC AGTTCTATTA TACATAAATC TGTAT-
TCATC TGGATCTTCA CAATTAGTAT 4920
AACAAAATTT ACAAATTTTC CACATAGTTT
TAAAGGGCTT TCCATTCATA TTCCATGCAT 4980
TAAATTCATC AGTATCATAA GGGTCTCTAT GGT-
TAATTAA TTCTTTAAAA TAATACACAC 5040
ATTCTATCAG CATAGTTTCA TCTAACCATT CAGG-
TATTTC ATTTAAATGC ATAACAGCTA 5100
AATATAACTG GAAAGGTAAT CTGTTTTGTT TTGTC-
CAATC CCAGTGTTCT AATTCTTCCA 5160
TAGCTAAAGT ATGATCTATG TCTTCTCCAC AAG-
CAATAAT CTGATTATCT AGATCATGCT 5220
GCATATTAAG TATAGGTTTA GGCAAAATTG
ACAAGTCTAG ACCATTAAGT CTAGCAGTCT 5280
TATAAGCCTC ATAGAACAAA GACTTTGGAT TGTA-
CACTTT TTCAAATAAA CGAACGAACA 5340
CAAAGAAACC TGGCAATAGA CATACCGATT ATAT-
TCTGGA ACCACTTTTG CACAACACTA 5400
CTTTTTCACT GAGATGTTCA CTCGACGACT GCT-
GCTCGTA GACTGATGAT GGCGCTCTGC 5460
TGTTATCTCT ATTTATAGCC AATGGTCCGC TGGC-
CAGCCA CATCCTGTTT TGCACACGGC 5520
CCAGCCTCGA CGCGAGTTTG CCGGTCAAAC GAG-
GTCACAA TAACAAGATA ATAAAATGCG 5580
CATAAATTAT CTCAAGGTTT GTTTGCATGC
TATCTCTTYT ACTCATATTG CTATCTCGCT 5640
CTAACAGTTG CTATAGTGCT ATCTCACTCG CACAC-
TATTG CTGTCCTTCA CTAACATCAG 5700
GTCCTGTGTT CCACCTTCAG CTCCAAGGTC TTCG-
GATCCT CTCCATCATC AGGTCAGTAG 5760
ACCATCAGCT CAGAAGGTCA AAGGTCAGTA GAC-
CAGAAGG TCACAGAAGT AGGTCAAGGT 5820
CATATAGAAG GTCAAAGGTC AAGGTCACCG
TGACGTCATC AAGTACTCTA TACATGCTGA 5880
GTACTTGCTT ATACTCTACG AGTATTGCC (Z)$_p$ 5910
wherein N is A or C or G or T bases, wherein N is an integer from 0 to 50 at location 1 and 0 to 130 at location 5910 respectively and M at location 1657 is the base A or C and Y at location 5619 is the base C or T.

4. A sequence of the viral DNA of the Densovirus J-DNV (SEQ ID NO. 1) having the sequence as defined in claim 3 wherein n is 0 nucleotides in length.

5. A recombinant plasmid pBRJ capable of replicating itself in *E. coli* which contains the complete sequence of the viral genome of the Densovirus J-DNV as defined in claim 4.

6. An *Escherichia coli* host bacterium transformed by a plasmid as defined in claim 5.

\* \* \* \* \*